US009301721B2

(12) United States Patent
Dawson et al.

(10) Patent No.: US 9,301,721 B2
(45) Date of Patent: Apr. 5, 2016

(54) SIGNAL STABILIZATION IN A DIELECTRIC SENSOR ASSEMBLY

(71) Applicant: RESCON LTD, Farnborough (GB)

(72) Inventors: Thomas Andrew Dawson, Aldershot (GB); Robert Basil, Lawrenceville, GA (US)

(73) Assignee: RESCON LTD, Farnborough (GB)

( * ) Notice: Subject to any disclaimer, the term of this patent is extended or adjusted under 35 U.S.C. 154(b) by 292 days.

(21) Appl. No.: 13/846,347

(22) Filed: Mar. 18, 2013

(65) Prior Publication Data

US 2014/0218059 A1     Aug. 7, 2014

Related U.S. Application Data

(63) Continuation of application No. 13/835,762, filed on Mar. 15, 2013.

(60) Provisional application No. 61/759,827, filed on Feb. 1, 2013.

(51) Int. Cl.
*G01R 27/26* (2006.01)
*A61B 5/00* (2006.01)
*A61B 5/0408* (2006.01)
*A61B 5/0478* (2006.01)
*A61B 5/0492* (2006.01)

(52) U.S. Cl.
CPC ............ *A61B 5/7225* (2013.01); *A61B 5/0408* (2013.01); *A61B 5/0478* (2013.01); *A61B 5/0492* (2013.01); *A61B 2562/0214* (2013.01)

(58) Field of Classification Search
CPC ..................... A61B 5/7225; A61B 2562/0214; A61B 5/04–5/0496; G01N 27/22–27/24
See application file for complete search history.

(56) References Cited

U.S. PATENT DOCUMENTS

| | | | | |
|---|---|---|---|---|
| 4,994,793 A * | 2/1991 | Curtis | ............................ | 340/666 |
| 6,203,502 B1 * | 3/2001 | Hilgendorf et al. | ........... | 600/538 |
| 6,952,606 B2 | 10/2005 | Anderson et al. | | |
| 7,208,960 B1 * | 4/2007 | Deangelis et al. | ............. | 324/661 |
| 2001/0012384 A1 * | 8/2001 | Kalnitsky et al. | .............. | 382/124 |
| 2004/0267165 A1 * | 12/2004 | Sarvazyan et al. | ............. | 600/587 |
| 2005/0110103 A1 * | 5/2005 | Setlak | ............................ | 257/414 |
| 2008/0287767 A1 * | 11/2008 | Pasveer et al. | ................. | 600/372 |
| 2009/0254134 A1 | 10/2009 | Nikolov et al. | | |
| 2010/0160737 A1 | 6/2010 | Shachar et al. | | |
| 2011/0242048 A1 * | 10/2011 | Guedon et al. | ................ | 345/174 |
| 2011/0242050 A1 * | 10/2011 | Byun et al. | .................... | 345/174 |

(Continued)

OTHER PUBLICATIONS

Enabling Capacitive Touch, 2006, https://www.eecs.berkeley.edu/~boser/courses/40/labs/docs/MSP430%20touch%20pad%20slap105.pdf.*

(Continued)

*Primary Examiner* — Patrick Assouad
*Assistant Examiner* — Demetrius Pretlow
(74) *Attorney, Agent, or Firm* — Tillman Wright, PLLC; Chad D. Tillman; Jeremy C. Doerre

(57) ABSTRACT

A non-resistive contact sensor assembly includes an electric field sensor device, including a dielectric component for receiving an electrical signal from an object of interest and a signal processing component for processing the electrical signal, a voltage regulator for controlling voltage to the dielectric component and the signal processing component, and a common ground reference for the dielectric component and the signal processing component.

20 Claims, 6 Drawing Sheets

(56) References Cited

U.S. PATENT DOCUMENTS

| | | | |
|---|---|---|---|
| 2011/0267296 A1* | 11/2011 | Noguchi et al. | 345/173 |
| 2012/0162123 A1* | 6/2012 | Kent et al. | 345/174 |
| 2013/0135207 A1* | 5/2013 | Neil et al. | 345/168 |
| 2014/0062504 A1 | 3/2014 | Dawson | |
| 2014/0062505 A1 | 3/2014 | Dawson | |
| 2014/0062508 A1 | 3/2014 | Dawson | |
| 2014/0125358 A1 | 5/2014 | Dawson et al. | |
| 2014/0152319 A1 | 6/2014 | Dawson et al. | |
| 2014/0218058 A1 | 8/2014 | Dawson et al. | |

OTHER PUBLICATIONS

Digi-Key Iproving Touch Screen Performance by Good Design, 2011, http://www.digikey.com/en/articles/techzone/2011/sep/improving-touch-screen-performance-by-good-design.*

Capacitive Touch Sensing , Jan. 2013, http://www.ti.com.cn/cn/lit/an/slaa574/slaa574.pdf.*

Information Disclosure Statement (IDS) Letter Regarding Common Patent Applications(s), dated Aug. 14, 2014.

* cited by examiner

LAYER 1 (SIGNAL)

LAYER 2 (GROUND)

LAYER 3 (POWER)

LAYER 4 (SIGNAL)

SIGNAL STABILIZATION IN A DIELECTRIC SENSOR ASSEMBLY

CROSS-REFERENCE TO RELATED APPLICATIONS

The present application is U.S. continuation patent application of, and claims priority under 35 U.S.C. §120 to, U.S. nonprovisional patent application Ser. No. 13/835,762, filed Mar. 15, 2013, which patent application is incorporated by reference herein, and which application is itself a U.S. nonprovisional patent application of, and claims priority under 35 U.S.C. §119(e) to, U.S. provisional patent application Ser. No. 61/759,827 to Dawson, filed Feb. 1, 2013 and entitled "SIGNAL STABILIZATION IN A DIELECTRIC SENSOR ASSEMBLY," which '827 application is incorporated by reference herein in its entirety. Additionally, the entirety of each of the following co-pending, commonly-assigned U.S. patent applications, and any application publication thereof, is expressly incorporated herein by reference:

(a) U.S. provisional patent application Ser. No. 61/671,647 to Dawson, filed Jul. 13, 2012 and entitled "REDUCING MOVEMENT AND ELECTROSTATIC INTERFERENCE IN A NON-RESISTIVE CONTACT SENSOR ASSEMBLY;"

(b) U.S. provisional patent application Ser. No. 61/695,986 to Dawson, filed Aug. 31, 2012 and entitled "SIGNAL STABILIZATION IN A NON-RESISTIVE CONTACT SENSOR ASSEMBLY;"

(c) U.S. non-provisional patent application Ser. No. 13/834,664, filed Mar. 15, 2013, and entitled, "REDUCING MOVEMENT AND ELECTROSTATIC INTERFERENCE IN A NON-RESISTIVE CONTACT SENSOR ASSEMBLY;" and (d) U.S. non-provisional patent application Ser. No. 13/834,918, filed Mar. 15, 2013, and entitled, "SIGNAL STABILIZATION IN A NON-RESISTIVE CONTACT SENSOR ASSEMBLY."

STATEMENT REGARDING FEDERALLY SPONSORED RESEARCH OR DEVELOPMENT

This invention was made with government support under contract number W911NF-12-C-0004 awarded by DARPA. The government has certain rights in the invention.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

1. Field of the Present Invention

The present invention relates generally to electric field sensors, and, in particular, to signal stabilization in a non-contact resistive contact sensor assembly.

2. Background

Conventional electrodes act as a current transducer converting ionic currents into electronic ones so electrophysiological status can be assessed. The uses for this are many and broadly range from assessment of neural (EEG), and cardiac (ECG) and skeletal (EMG) muscle activity.

This approach requires conductive contact with the source and has inherent problems. The first of these is the requirement of clean skin exposure. This requirement may compromise continuous usability due to the effects of environmental contaminants, both on the skin and in the atmosphere; extremes of temperature and their resulting general effect on skin due to physiological reactions such as "goose bumps" and excessive sweating as well as other phenomena; and potential reactions to conductive materials. The process of preparing skin and securing a good conductive contact can also decrease compliance, especially in if intended for continuous day to day use. Furthermore, during exercise, the physicality can result in electrodes being displaced. Other issues include shorting between electrodes, especially when placed in close proximity to each other, and charge transfer which has potential safety implications as well as the issue of the measurement process corrupting the signal.

The problems, outlined above, may be at least partially solved by the use of capacitive electrodes (non-resistive contact sensors) as they acquire signals through capacitive coupling, not requiring resistive contact with the source. They provide many benefits, including the fact that no electrical contact is required, and so no skin preparation or conducting pads are necessary and they can be readily moved or relocated to get an optimal signal. In addition, they can be miniaturized, they have very low power requirements, and they can be embodied as passive electric field sensors with the result that adjacent sensors do not interfere with each other.

The use of capacitive electrodes for electrophysiological monitoring is not a recent innovation, with Richardson describing it for acquisition of the cardiac signal in 1967 (see *The insulated electrode: a pasteless electrocardiographic technique*. Richardson P C. Proc. Annu. Conf. on Engineering in Medicine and Biology 7: 9-15(1967)). This system was, however, flawed being prone to problems including poor signal to noise ratio, voltage drift, electrostatic discharge and parasitic capacitance. These are still problems with capacitive sensor technologies today. Many of those problems have been addressed, at least partially, but problems with signal stability interference still plague this technology. Signal stability interference is especially problematic during movement. Movement may lead to a variety of issues that may compromise continuous signal acquisition including contact electrification between the body surface and the sensor electrode; charge build-up on the body resulting in baseline shift and potential saturation if occurs too rapidly; and movement of the sensor relative to the body that can also lead to baseline shift and saturation (railing).

When dry contact electrodes are placed in direct contact with a person, and particularly when they are moved, triboelectric effects (electrical charges created by sliding friction and pressure) are frequently generated. Triboelectric effects of this nature may cause contact electrification where static charges may be delivered to the pick-up electrode. This static charge can produce a near-direct current (DC) or very low frequency drift in the sensor that may interfere with the physiological alternating current (AC) signal that is being measured or may saturate the sensor causing railing, after which the sensor takes time to return to being able to produce a useful physiologically-relevant output. If the electrode moves relative to the body, it will also pick up a geoelectric displacement signal. That is, the effect of the body, an electrically active structure, moving through the geoelectric field, which is on the order of $100\,Vm^{-1}$, will cause relative polarization of the sensor that will displace the baseline and may cause the sensor to saturate. An additional source of interference is that of clothing moving on the body. As clothing moves on the body, charge separation can occur when materials that are separated on the triboelectric series donate or receive electrons from each other. After a material becomes charged it may discharge onto the surface where an electric potential is being measured, thereby interfering with signal acquisition.

Various issues can arise as a result of these various forms of interference. For example, issues may arise in the signal acquisition phase due to corruption of the signal from local electrical activity, in the signal referencing phase due to poor referencing of the signal to an appropriate earth, and during the transfer of the signal to processing units where the signal may be susceptible to interference. Thus, a need exists for devices, methods, and/or systems for reducing interference and stabilizing the signals being acquired and processed.

SUMMARY OF THE PRESENT INVENTION

Broadly defined, the present invention according to one aspect is a non-resistive contact sensor assembly, including: an electric field sensor device, including a dielectric component for receiving an electrical signal from an object of interest and a signal processing component for processing the electrical signal; a voltage regulator for controlling voltage to the dielectric component and the signal processing component; and a common ground reference for the dielectric component and the signal processing component.

In a feature of this aspect, the dielectric component includes an active component and a neutral component.

In another feature of this aspect, the signal processing component includes an A/D converter for converting the electrical signal received from the object of interest to a digitized signal.

In a further feature, the signal processing component includes an analog filter for tuning the electrical signal received from the object of interest prior to the conversion of the electrical signal to a digitized signal by the A/D converter. In still further features, the dielectric component, analog filter and A/D converter share a common ground reference; the analog filter and the A/D converter share a common voltage reference; the signal processing component includes a level shift buffer between the analog filter and the A/D converter; and/or the analog filter, the level shift buffer, and the A/D converter share a common voltage reference.

In a further feature, the A/D converter is less than 50 mm away from the dielectric component. In a still further feature, the A/D converter is less than 20 mm away from the dielectric component. In a still further feature, the A/D converter is less than 10 mm away from the dielectric component. In a still further feature, the A/D converter is electrically connected to a dielectric component signal output by a signal connection that is less than 10 mm in length.

In a further feature, the A/D converter oversamples the electrical signal at a rate of at least 16 times per sample to enhance signal clarity. In a still further feature, the A/D converter oversamples the electrical signal at rate of at least 128 times per sample.

In another feature of this aspect, the circuitry has a ground plane top layer, a ground plane bottom layer, and at least a partial ground plane in all layers directly below the dielectric component.

In another feature of this aspect, the non-resistive contact sensor assembly further includes a casing in which the signal processing component is surrounded or embedded and wherein the common ground reference is connected to the casing and to the dielectric component.

In another feature of this aspect, circuitry providing voltage and ground reference for the components is implemented in a circuit board.

In another feature of this aspect, circuitry providing voltage and ground reference for the components is implemented in an Application-Specific Integrated Circuit (ASIC).

In another feature of this aspect, circuitry providing voltage and ground reference for the components is implemented in a combination of a circuit board with ASIC components.

In another feature of this aspect, circuitry providing voltage and ground reference for the components is implemented in a package that physically resembles a single component.

In another feature of this aspect, the neutral component includes a dielectric membrane that interacts with the electric field to pick up the electrical signal from the object of interest.

Broadly defined, the present invention according to another aspect is a non-resistive contact sensor assembly, including: an electric field sensor device, including a dielectric component for receiving an electrical signal from an object of interest and an A/D converter for converting the electrical signal received from the object of interest to a digitized signal; and circuitry interconnecting the dielectric component and the A/D converter and including a layer, directly below the dielectric component, that is substantially entirely ground fill.

In a feature of this aspect, the dielectric component includes an active component and a neutral component.

In another feature of this aspect, the non-resistive contact sensor assembly further includes an analog filter for tuning the electrical signal received from the object of interest prior to the conversion of the electrical signal to a digitized signal by the A/D converter. In further features, the dielectric component, analog filter and A/D converter share a common ground reference; the analog filter and the A/D converter share a common voltage reference; the signal processing component includes a level shift buffer between the analog filter and the A/D converter; and/or the analog filter, the level shift buffer, and the A/D converter share a common voltage reference.

In another feature of this aspect, the A/D converter is less than 50 mm away from the dielectric component. In a further feature, the A/D converter is less than 20 mm away from the dielectric component. In a still further feature, the A/D converter is less than 10 mm away from the dielectric component. In a still further feature, the A/D converter is electrically connected to a dielectric component signal output by a signal connection that is less than 10 mm in length.

In another feature of this aspect, the A/D converter oversamples the electrical signal at a rate of at least 16 times per sample to enhance signal clarity. In a further feature, the A/D converter oversamples the electrical signal at rate of at least 128 times per sample.

In another feature of this aspect, the circuitry has a ground plane top layer, a ground plane bottom layer, and at least a partial ground plane in all layers directly below the dielectric component.

In another feature of this aspect, the non-resistive contact sensor assembly further includes a casing in which the signal processing component is surrounded or embedded and wherein a common ground reference is connected to the casing and to the dielectric component.

In another feature of this aspect, circuitry providing voltage and ground reference for the components is implemented in a circuit board.

In another feature of this aspect, circuitry providing voltage and ground reference for the components is implemented in an Application-Specific Integrated Circuit (ASIC).

In another feature of this aspect, circuitry providing voltage and ground reference for the components is implemented in a combination of a circuit board with ASIC components.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1A:
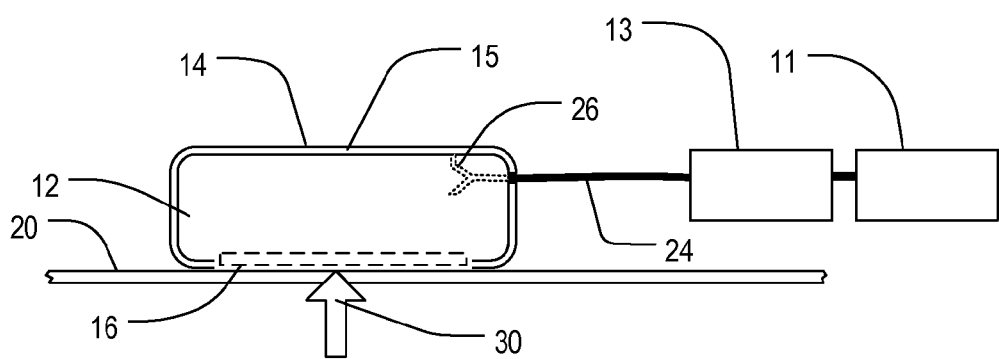
FIG. 1A is a schematic diagram of a non-resistive contact sensor assembly in accordance with one or more preferred embodiments of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

In various aspects, the present invention relates to methods of attenuating or eliminating unwanted movement or electrostatic interference on signals acquired via non-resistive contact sensors from various entities, both biological and other. Such sensors may be used by themselves, or may be used in combination with other sensors. The sensor data is utilized for detecting properties of the entities.

For biological entities, the invention utilizes an electric field sensor or sensors for the measurement of the structural and functional characteristics of organs and other structures where the electric field sensor does not have resistive contact with the organism, conferring multiple advantages. In various aspects, the present invention relates to sensors, sensor housings, fastenings and sensor systems including devices and installations for assemblies for detecting structural and functional signatures associated with electric potentials that may detect a displacement signature within the geomagnetic field, and/or specific components and/or structures that are a component of that entity or entities. There is preferably no resistive contact between the entity and the signal transduction component of the electric field sensor or sensors. Other sensor types may be added in to provide further information, such as for the identification and elimination or attenuation of unwanted electrostatic or movement signal associated with the recording of non-resistive contact electric fields from that entity, in whatever state, such as during active or passive movement.

In particular, the present invention, in various aspects, relates to novel methods and apparatuses for stabilizing the target signal when using an electric field sensor or sensors of the type that does not have resistive contact with the entity, generally an organism, which is being monitored. In various aspects, the invention relates to combinations and permutations of: an electric field sensor device, including a dielectric component for receiving an electrical signal from an object of interest; a signal processing component, that may include an A/D converter for converting the electrical signal received from the object of interest to a digitized signal; a voltage regulator for controlling voltage to the dielectric component and the signal processing component; a common ground reference for the dielectric component and the signal processing component; and/or circuitry interconnecting the dielectric component and the A/D converter and including a layer, directly below the dielectric component, that is substantially entirely ground fill. Other features and aspects relate to combinations and permutations with any of the foregoing and applying an electric field to electrically stabilize the sensor zone; the use of a conductive casing to act as a reference for the signal that is being acquired; the use of an analog to digital converter in the sensor head to digitally fix the signal; the use of a barrier (guard or shield) between the analog to digital converter to mitigate signal corruption the converter; a logic board to process the signal in the sensor head; a compressive material or spring from another fixed structure, such as a helmet, to hold the referencing component and/or the electrode firmly on the surface of the entity being measured; a cable or wireless transmitter to transmit the digitized signal; and/or a resistive contact electrode that may be incorporated into the reference casing or used as a separate component to add signal acquisition resilience.

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

FIG. 1A is a schematic diagram of a non-resistive contact sensor assembly 10 in accordance with one or more preferred embodiments of the present invention. The sensor assembly 10 includes at least one sensor head 12, a power supply 11, and a primary voltage regulator 13. In at least some embodiments, the power supply 11 and voltage regulator 13 are external to the sensor head 12 but electrically connected by a power and data cable 24. Each sensor head 12 includes at least one electric field sensor device 16. In at least some embodiment, the electric field sensor device 16 is a dielectric component. The dielectric component 16 is at least partially surrounded by, or embedded in, a housing 14, at least portions of which may be made of anti-triboelectric material. The housing 14 may include a conductive casing (shielding) 15 that makes direct resistive contact with the skin or other surface 20 on which the sensor assembly 10 is placed but is electrically isolated from the dielectric component 16. The casing 15 may be grounded by a ground connection 26 to the power and data cable 24 to the unit 10. The casing 15 may thus serve as a reference with regard to a target signal 30 from the object of interest.

In various respects, the sensor assembly 10 and sensor head 12, and dielectric component or other electric field sensor device 16 may have one or more characteristics described in the '664 application or described in the '918 application.

Figure 1B:
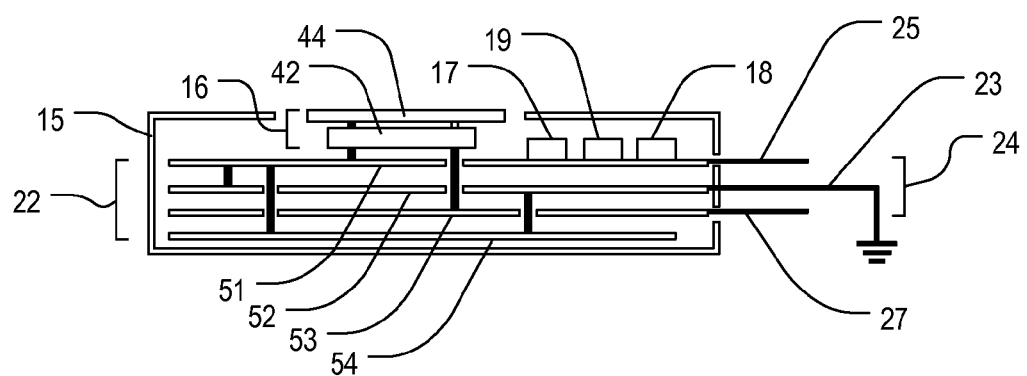
FIG. 1B is a schematic diagram of the sensor head of FIG. 1A, shown in an inverted configuration.

FIG. 1B is a schematic diagram of the sensor head 12 of FIG. 1A, shown in an inverted configuration. Each sensor head 12 further includes one or more signal processing component 17,18,19, an optional secondary voltage regulator (not shown), circuitry 22 interconnecting the other components as well as providing voltage and ground reference for the other components, and a power and data cable 24. The power and data cable 24 may include a ground connection 23, a signal connection 25, and a power connection 27. The circuitry 22, which may be implemented on a printed circuit board or the like, interconnects the components, provides proper voltage levels from the voltage regulator or regulators, and provides a reference ground for the dielectric component 16 and various other components.

Figure 2:
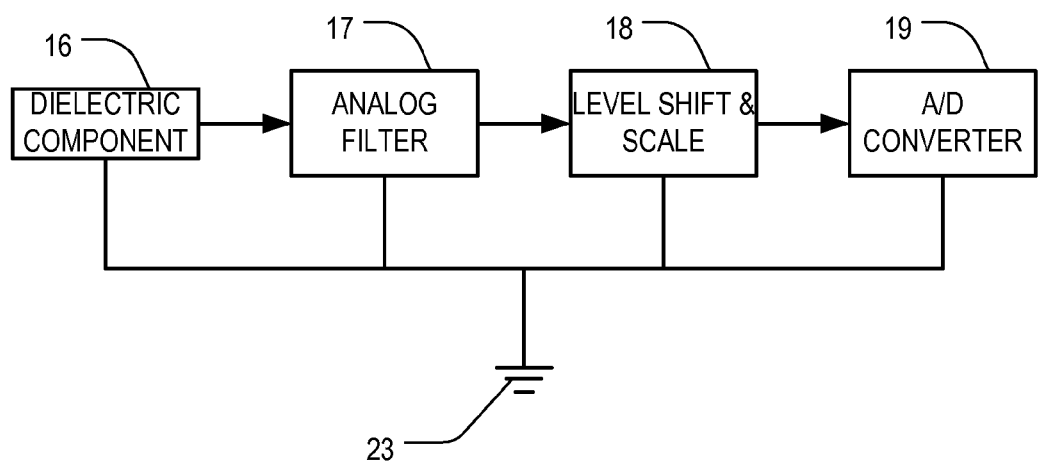
FIG. 2 is a block diagram of portions of the sensor head of FIG. 1B, illustrating signal processing of the amplified signal from the sensor device.

FIG. 2 is a block diagram of portions of the sensor head 12 of FIG. 1B, illustrating signal processing of the amplified signal from the dielectric component 16. After the signal from the electrode 16 is amplified, the resulting signal may be processed by the signal processing components 17,18,19. Such components may include an analog filter 17 for tuning the signal of interest, a level shift and scale circuit 19, including a buffer, that adjusts the resulting levels as desired, or an A/D converter 18 for converting the output to a digital signal. As shown in FIG. 2, in at least some embodiments, a common reference ground 23 is provided to each of the dielectric component 16, the analog filter 17, the level shift and scale circuit 19, and the A/D converter 18.

The A/D converter 18 preferably oversamples at a rate of at least 16 times per sample, and still more preferably oversamples at a rate of at least 128 times per sample, in order to enhance signal clarity. In at least some embodiments, samples are taken 1000 times per second, so 16 times oversampling (i.e., oversampling at a rate of 16 times per sample) would result in 16,000 total samples, and 128 times oversampling (i.e., oversampling at a rate of 128 times per sample) would result in 128,000 total samples. In at least some of these embodiment, the oversampling is controlled such that data transfer operations and other operations are not occurring at the same time, thereby reducing or minimizing noise around the dielectric component 16. Furthermore, in at least some embodiments, the A/D converter 18 is located less than 50 mm away from the dielectric component 16 at least for a purpose of reducing or minimizing risk of unwanted parasitic capacitance. In at least some of these embodiments, the A/D converter 18 is located less than 20 mm, and preferably less than 10 mm, away from the dielectric component 16. In particular, the electrical connections for the signals between the signal outputs of the dielectric component 16 and the signal inputs of the A/D converter 18 are preferably less than 10 mm in length. Finally, in at least some embodiments, more than one sensor head 12, more than one dielectric component 16 in each sensor head 12, or both, are utilized, and their outputs are coordinated. In at least some of these embodiments, the dielectric components 16 are synchronized so that they are both sampling at the same time and transferring data at the same time.

In at least some embodiments, the electric field sensor device 16 of the sensor head 12 is a dielectric component 16 is made up of an active component 42 and a neutral component 44. The active component 42 may include an ultrahigh impedance amplifier, high and low pass filters, and well controlled input bias with active guarding and shielding all around. The neutral 44 component may include a dielectric membrane that interacts with the electric field to pick up the signal, which is then amplified. This dielectric component 16 generally (and the dielectric membrane particularly) may or may not be exposed to the exterior of the housing 14, but is preferably capacitively coupled to the skin or other surface 20 of the entity being analyzed. In at least some embodiments, the dielectric component 16 is arranged to have direct physical contact with the skin or other surface 20 on which the sensor assembly 10 is placed.

In at least some embodiments, some or all of the signal processing is carried out within the confines of the sensor casing 15, and in at least some embodiments, the amplification is likewise carried out within the confines of the sensor casing 15. In at least some embodiments, the signal processing components 17,18,19 is also shielded from the electrode 16 itself by the circuitry 22, which may serve as an internal partition providing an electrical field barrier against the electrode 16 and the amplification thereof. In this regard, it will be appreciated that in at least some embodiments, amplification likewise takes place on the opposite side of the circuitry 22 from the A/D converter 18 and other signal processing components. Advantageously, the shielding offered by the partition 22 helps to prevent the A/D converter 18 and other components from being affected by interference caused by various electrical effects.

Figure 3:
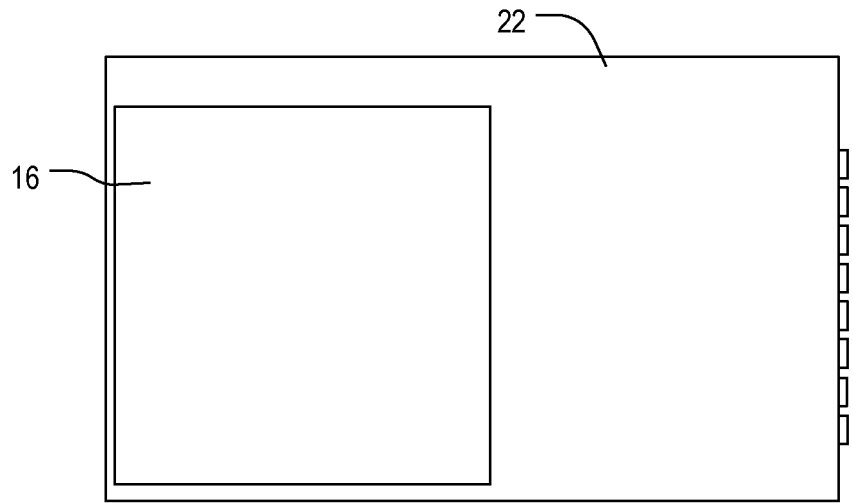
FIG. 3 is an enlarged top view of an exemplary implementation of the dielectric component and circuitry of FIG. 1B.

FIG. 3 is an enlarged top view of an exemplary implementation of the dielectric component 16 and circuitry 22 of FIG. 1B. In this exemplary implementation, the dielectric component 16 is carried on a four-layer printed circuit board 22. It will be appreciated however, that the semiconductor device 22 may be implemented in a variety of physical forms, including a standalone circuit board, as an application-specific integrated circuit or "ASIC," or the like.

Figure 4A:
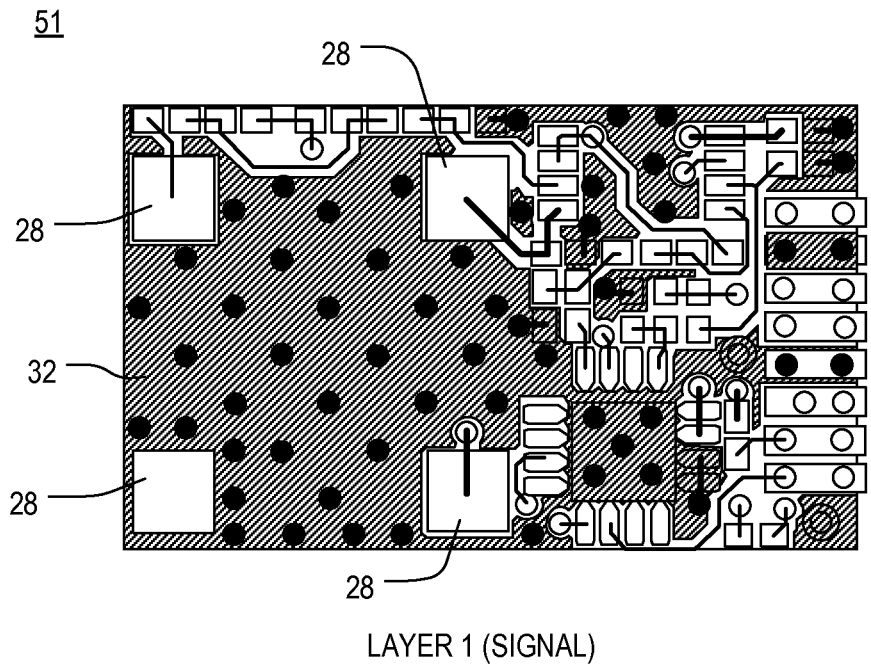
FIG. 4A is a physical circuit diagram of layer 1 of the printed circuit board of FIG. 3.
Figure 4B:
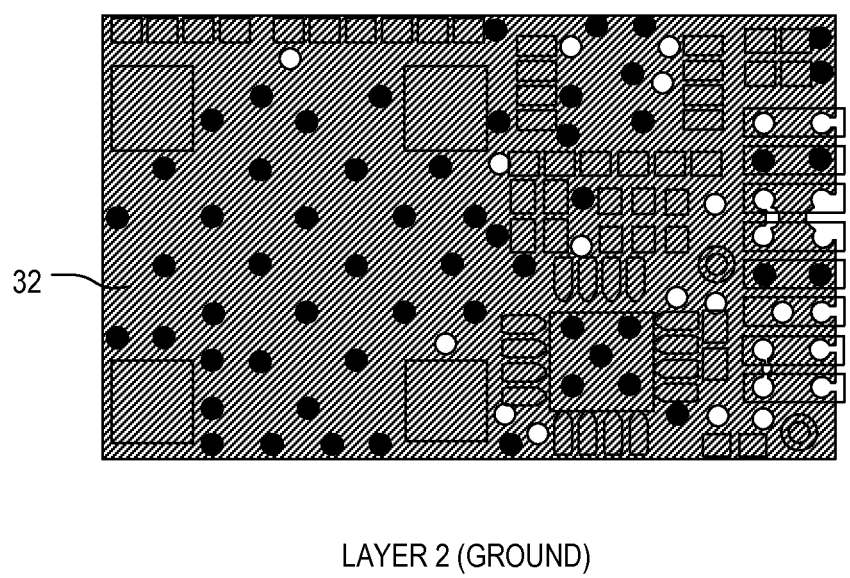
FIG. 4B is a physical circuit diagram of layer 2 of the printed circuit board of FIG. 3.
Figure 4C:
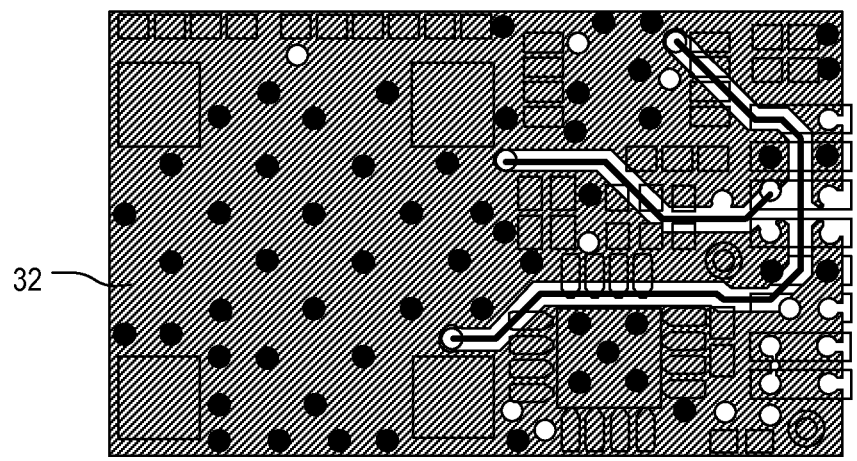
FIG. 4C is a physical circuit diagram of layer 3 of the printed circuit board of FIG. 3.
Figure 4D:
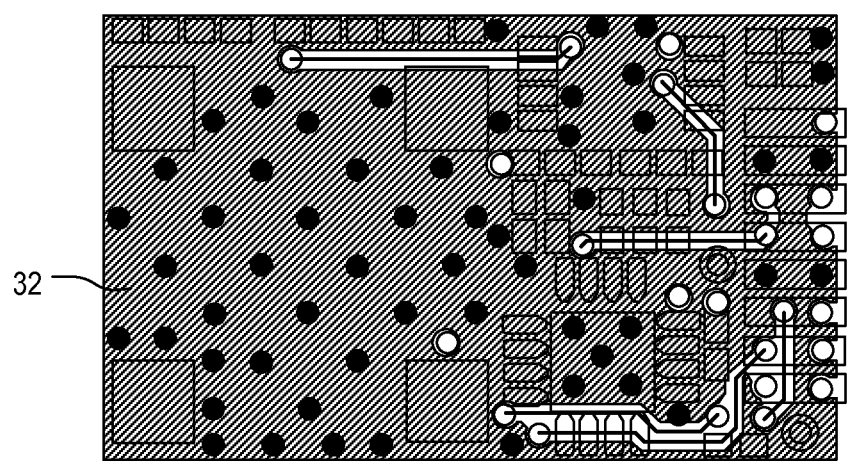
FIG. 4D is a physical circuit diagram of layer 4 of the printed circuit board of FIG. 3.

FIG. 4A is a physical circuit diagram of layer 1 51 of the printed circuit board 22 of FIG. 3; FIG. 4B is a physical circuit diagram of layer 2 52 of the semiconductor device 22 of FIG. 3; FIG. 4C is a physical circuit diagram of layer 3 53 of the printed circuit board 22 of FIG. 3; and FIG. 4D is a physical circuit diagram of layer 4 54 of the semiconductor device 22 of FIG. 3. In some ways, layers 1 and 4 may be considered as signal layers or planes (i.e., layers used primarily for routing signal wires), while layer 2 may be considered as a ground plane (i.e., a layer used primarily for routing ground wires) and layer 3 may be considered as a power plane (i.e., a layer used primarily for routing power wires). The four large squares in the left half of each layer are the mounting pads for the dielectric component 16. Small circles represent vias connecting one layer to another, with black circles generally showing ground connections from the ground plane to other planes and white circles generally showing other connections between planes. Squares, rectangles, and other shapes generally represent devices, pads, and the like, and are mostly located on layer 1. Wires connecting vias, devices, pads, and the like together are generally represented by black lines, with the thickest black lines generally represent voltage controlled power supply connections being distributed from the power plane.

Perhaps most notably, the grey, cross-hatched areas represent ground fill 32. Nearly all of layer 2 (the ground plane) is occupied by such fill 32, which may for example be a continuous layer of metal, with the only exceptions being vias passing through layer 2 for power and signal connections between layer 1 and layers 3 and 4. However, the other layers all include large expanses of such fill 32 as well. For example, ground fill 32 occupies all of layer 3, with the only exceptions being vias passing therethrough, for power and signal connections between layer 3 and layers 1 and 4, and power wires being routed in layer 3 for distribution to layers 1 and 4. Similarly, ground fill 32 occupies all of layer 4, with the only exceptions being vias passing therethrough for power and signal connections between layer 4 and layers 1 and 3, and signal wires being routed in layer 4 for distribution to layer 1. Even the main signal plane, layer 1, has large areas of ground fill 32 between various devices, pads, signal wiring, power wiring, and the like, including substantially all of the area beneath the dielectric component 16 (i.e., the area between the four large mounting pads). All of these areas of ground fill 32 are tied together at numerous locations by vias (represented by the small black circles), thereby ensuring a consistent and uniform ground connection for all active components. It will be appreciated that because of the large areas of ground fill 32 in the signal and power planes, and particularly in layers 3 and 4, these planes can in some contexts be described as "ground planes" themselves.

Various advantages may be achieved using one or more of the foregoing embodiments of the present invention. The robustness of the measurement of the electrical signature of an entity or sub-component of that entity may be increased. A signal being measured or analyzed may be protected closer to the source, thereby protecting it from corruption. The stability of the signal may be enhanced. The signal-to-noise ratio for an electric field sensor may be enhanced. The effect of electrostatic charge interference with an electric field sensor may be minimizes or eliminated entirely. The use of electric field sensors during exercise and daily activities may be increased, as can the usability of electric field sensors with different types of clothing and when clothing is moving due to exercise or external forces (like wind). Similarly, the usability of electric field sensors may be increased when there is external contact that would otherwise knock the sensor loose or that would result in charge transfer to the entity being measured or analyzed. Conversely, the likelihoods of contact electrification, sensor DC drift, and sensor saturation may all be decreased.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A non-resistive contact sensor assembly, comprising:
an electric field sensor device, including a dielectric component for receiving an electrical signal from an object of interest and an A/D converter for converting the electrical signal received from the object of interest to a digitized signal;

circuitry interconnecting the dielectric component and the A/D converter and including a layer, directly below the dielectric component, that is substantially ground fill, the circuitry shielding the A/D converter from the dielectric component and serving as an internal partition providing an electrical field barrier against the dielectric component; and a fastening for fastening the non-resistive contact sensor assembly to an organism for measurement of characteristics of an organ of the organism.

2. The non-resistive contact sensor assembly of claim 1, wherein the dielectric component includes an active component and a neutral component.

3. The non-resistive contact sensor assembly of claim 2, further comprising an analog filter for tuning the electrical signal received from the object of interest prior to the conversion of the electrical signal to a digitized signal by the A/D converter.

4. The non-resistive contact sensor assembly of claim 3, wherein the dielectric component, analog filter and A/D converter share a common ground reference.

5. The non-resistive contact sensor assembly of claim 3, wherein the analog filter and the A/D converter share a common voltage reference.

6. The non-resistive contact sensor assembly of claim 3, wherein the signal processing component includes a level shift buffer between the analog filter and the A/D converter.

7. The non-resistive contact sensor assembly of claim 6, wherein the analog filter, the level shift buffer, and the A/D converter share a common voltage reference.

8. The non-resistive contact sensor assembly of claim 2, wherein the A/D converter is less than 50 mm away from the dielectric component.

9. The non-resistive contact sensor assembly of claim 8, wherein the A/D converter is less than 20 mm away from the dielectric component.

10. The non-resistive contact sensor assembly of claim 9, wherein the A/D converter is less than 10 mm away from the dielectric component.

11. The non-resistive contact sensor assembly of claim 10, wherein the A/D converter is electrically connected to a dielectric component signal output by a signal connection that is less than 10 mm in length.

12. The non-resistive contact sensor assembly of claim 2, wherein the A/D converter oversamples the electrical signal at a rate of at least 16 times per sample to enhance signal clarity.

13. The non-resistive contact sensor assembly of claim 12, wherein the A/D converter oversamples the electrical signal at rate of at least 128 times per sample.

14. The non-resistive contact sensor assembly of claim 2, wherein the circuitry has a ground plane top layer, a ground plane bottom layer, and at least a partial ground plane in all layers directly below the dielectric component.

15. The non-resistive contact sensor assembly of claim 2, further comprising a casing in which the signal processing component is surrounded or embedded and wherein a common ground reference is connected to the casing and to the dielectric component.

16. The non-resistive contact sensor assembly of claim 2, wherein circuitry providing voltage and ground reference for the components is implemented in a circuit board.

17. The non-resistive contact sensor assembly of claim 2, wherein circuitry providing voltage and ground reference for the components is implemented in an Application-Specific Integrated Circuit (ASIC).

18. The non-resistive contact sensor assembly of claim 2, wherein circuitry providing voltage and ground reference for the components is implemented in a combination of a circuit board with ASIC components.

19. A non-resistive contact sensor assembly, comprising:
an electric field sensor device, including a dielectric component for receiving an electrical signal from an object of interest and an A/D converter for converting the electrical signal received from the object of interest to a digitized signal;
circuitry interconnecting the dielectric component and the A/D converter and including a layer, directly below the dielectric component, that is substantially entirely ground fill, the circuitry shielding the A/D converter from the dielectric component and serving as an internal partition providing an electrical field barrier against the dielectric component and amplification thereat; and
a fastening for fastening the non-resistive contact sensor assembly to an organism for measurement of characteristics of an organ of the organism.

20. A non-resistive contact sensor assembly, comprising:
an electric field sensor device, including a dielectric component for receiving an electrical signal from an object of interest and an A/D converter for converting the electrical signal received from the object of interest to a digitized signal, the dielectric component comprising an amplifier;
circuitry interconnecting the dielectric component and the A/D converter and including a layer, directly below the dielectric component, that is substantially entirely ground fill, the circuitry shielding the A/D converter from the dielectric component and serving as an internal partition providing an electrical field barrier against the dielectric component and amplification thereat; and
a fastening for fastening the non-resistive contact sensor assembly to an organism for measurement of characteristics of an organ of the organism.

* * * * *